United States Patent
Swanson et al.

(10) Patent No.: US 7,103,413 B2
(45) Date of Patent: Sep. 5, 2006

(54) FERRITE CORE TELEMETRY COIL FOR IMPLANTABLE MEDICAL DEVICE

(75) Inventors: Lawrence Swanson, Lino Lakes, MN (US); Jeffrey A. Von Arx, Minneapolis, MN (US); Ron Balczewski, Roseville, MN (US); Jeff Taylor, Wyoming, MN (US); Greg Carpenter, Centerville, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 285 days.

(21) Appl. No.: 10/194,401

(22) Filed: Jul. 12, 2002

(65) Prior Publication Data

US 2004/0010296 A1    Jan. 15, 2004

(51) Int. Cl.
    *A61B 18/04* (2006.01)
(52) U.S. Cl. .................................. 607/32; 128/903
(58) Field of Classification Search ............ 607/30–33, 607/60, 5, 9; 604/891.1; 128/903
    See application file for complete search history.

(56) References Cited

U.S. PATENT DOCUMENTS

| | | | |
|---|---|---|---|
| 3,667,477 A * | 6/1972 | Susset et al. .................. | 607/40 |
| 4,230,128 A | 10/1980 | Aramayo | |
| 4,262,632 A | 4/1981 | Hanton et al. | |
| 4,556,063 A | 12/1985 | Thompson et al. | |
| 4,562,841 A | 1/1986 | Brockway et al. | |
| 4,580,950 A * | 4/1986 | Sumikawa et al. ......... | 417/295 |
| 5,058,581 A | 10/1991 | Silvian | |
| 5,113,869 A | 5/1992 | Nappholz et al. | |
| 5,127,404 A | 7/1992 | Wyborny et al. | |
| 5,314,453 A | 5/1994 | Jeutter | |
| 5,337,756 A | 8/1994 | Barbier et al. | |
| 5,342,408 A | 8/1994 | deCoriolis et al. | |
| 5,385,578 A * | 1/1995 | Bush et al. .................. | 607/122 |
| 5,534,019 A * | 7/1996 | Paspa .......................... | 607/38 |
| 5,556,421 A * | 9/1996 | Prutchi et al. ................ | 607/36 |
| 5,562,713 A | 10/1996 | Silvian | |
| 5,683,432 A | 11/1997 | Goedeke et al. | |
| 5,735,887 A | 4/1998 | Barreras, Sr. et al. | |
| 5,749,912 A * | 5/1998 | Zhang et al. .................. | 607/57 |
| 5,861,019 A | 1/1999 | Sun et al. | |
| 5,862,803 A | 1/1999 | Besson et al. | |
| 5,876,331 A * | 3/1999 | Wu et al. ..................... | 600/139 |
| 5,957,854 A | 9/1999 | Besson et al. | |
| 6,009,350 A | 12/1999 | Renken | |
| 6,115,634 A | 9/2000 | Donders et al. | |
| 6,115,636 A | 9/2000 | Ryan | |
| 6,169,925 B1 | 1/2001 | Villaseca et al. | |
| 6,456,256 B1 | 9/2002 | Amundson et al. | |
| 6,505,072 B1 * | 1/2003 | Linder et al. .................. | 607/32 |
| 6,505,077 B1 * | 1/2003 | Kast et al. ..................... | 607/61 |
| 6,574,508 B1 * | 6/2003 | Zaouali et al. ................ | 607/36 |
| 6,766,200 B1 * | 7/2004 | Cox ............................ | 607/60 |
| 6,809,701 B1 * | 10/2004 | Amundson et al. ......... | 343/873 |

* cited by examiner

*Primary Examiner*—Mark Bockelman
(74) *Attorney, Agent, or Firm*—Schwegman, Lundberg, Woessner & Kluth, P.A.

(57) ABSTRACT

An implantable medical device such as a cardiac pacemaker with a telemetry coil located in the device header rather than the conductive housing. The telemetry coil has a core made of magnetically permeable material such as ferrite in order to increase the efficiency of the coil and lessen space requirements.

14 Claims, 4 Drawing Sheets

FERRITE CORE TELEMETRY COIL FOR IMPLANTABLE MEDICAL DEVICE

FIELD OF THE INVENTION

This invention pertains to implantable medical devices such as cardiac pacemakers and implantable cardioverter/defibrillators. In particular, the invention relates to an apparatus and method for enabling radio-frequency telemetry in such devices.

BACKGROUND

Implantable cardiac devices include devices which monitor heart activity and/or provide corrective therapy to the heart in the form of applied electrical energy. Examples of implantable cardiac devices include cardiac rhythm management devices such as pacemakers and implantable cardioverter/defibrillators. These devices are designed to be small in size and implanted beneath the skin of a patient. The device establishes electrical contact with the heart by one or more electrical leads having electrodes implanted within the heart, attached to the surface of the heart, or disposed subcutaneously and spaced from the heart.

Implantable cardiac devices commonly have the capability to communicate data with a device called an external programmer or other non-implanted device via a radio-frequency telemetry link. A clinician may use such an external programmer to program the operating parameters of an implanted medical device. For example, the pacing mode and other operating characteristics of a pacemaker are typically modified after implantation in this manner. Modern implantable devices also include the capability for bidirectional communication so that information can be transmitted to the programmer from the implanted device. Among the data which may typically be telemetered from an implantable device are various operating parameters and physiological data, the latter either collected in real-time or stored from previous monitoring operations.

Telemetry systems for implantable medical devices utilize radio-frequency energy to enable bidirectional communication between the implantable device and an external programmer. An exemplary telemetry system for an external programmer and a cardiac pacemaker is described in U.S. Pat. No. 4,562,841, issued to Brockway et al. and assigned to Cardiac Pacemakers, Inc., the disclosure of which is incorporated herein by reference. A radio-frequency carrier is modulated with digital information, typically by amplitude shift keying where the presence or absence of pulses in the signal constitute binary symbols or bits. The external programmer transmits and receives the radio signal with an antenna incorporated into a wand which can be positioned in proximity to the implanted device. The implantable device generates and receives the radio signal by means of an antenna that can be formed by a wire coil inside of the device housing.

Power for the device is supplied solely by a self-contained battery, and when the battery is exhausted a re-implantation procedure must be performed. Power for telemetry represents a significant overhead that shortens battery life. A typical bradycardia pacemaker, for example, may draw a total system current of 18 microamps with 15 microamps consumed by telemetry when the device is communicating with an external programmer. It is an objective of the present invention to provide a method and apparatus that enables more efficient telemetry.

SUMMARY OF THE INVENTION

The efficiency of a telemetry system may be described in terms of its energy cost per unit of transmitted information. One of the factors affecting efficiency is the bandwidth or maximum possible data rate of the telemetry system. Implantable cardiac devices are enclosed by a metallic housing, usually made of titanium in order to be biocompatible. A telemetry coil for inductive coupling with an external coil may also be enclosed within the metallic housing. Metals, however, act as a low-pass filter for electromagnetic energy which decreases the bandwidth of the telemetry system. The efficiency of a telemetry coil in an implantable device is therefore increased if the coil is located in a non-conductive header rather than within the metallic housing. This, however, necessitates that a smaller antenna be used because of the space constraints within the header. The size of a telemetry coil also affects telemetry efficiency because a smaller antenna radiates and receives electromagnetic energy less effectively than does a larger antenna. In order to lessen the space requirements of the telemetry coil and further increase its efficiency, the coil may be constructed with a core made of ferrite or other magnetically permeable material. Because ferrite is not a biocompatible material, and the header is not hermetically sealed, the core or the entire telemetry coil may be encapsulated in polyurethane.

DETAILED DESCRIPTION

Figure 1:
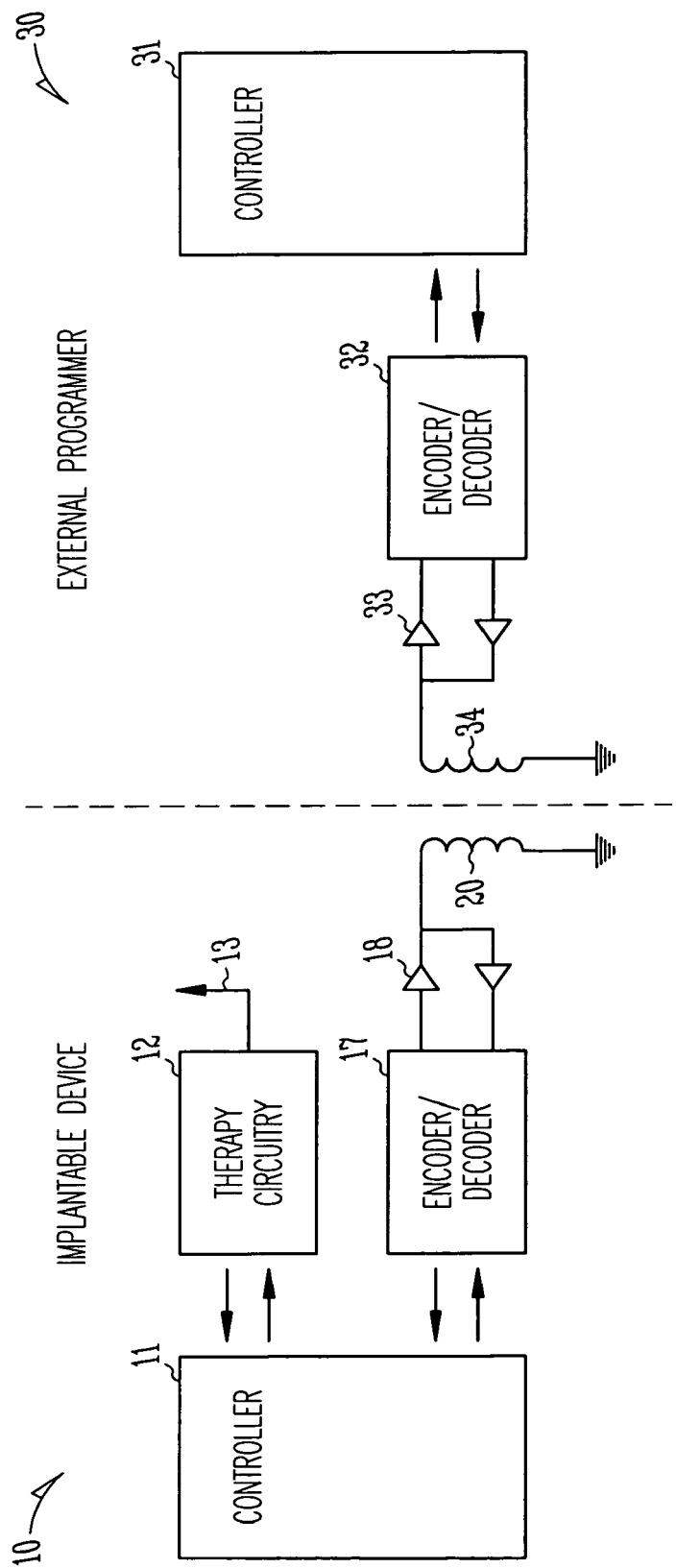
FIG. 1 shows the basic components of a telemetry system for a cardiac rhythm management device.

Implantable devices such as pacemakers and cardioverter/defibrillators are usually implanted subcutaneously or submuscularly on a patient's chest with leads threaded intravenously to the heart. FIG. 1 shows some of the basic components of an exemplary implantable cardiac rhythm management device 10 such as a pacemaker or cardioverter/defibrillator and an associated external programmer 30. The implantable device 10 includes a controller 11, such as a microprocessor and associated logic circuitry, which is interfaced to therapy circuits 12 for delivering electrical stimulation in the form of pacing pulses or shock pulses to the heart and for sensing cardiac activity. External lead wires 13 connect the therapy circuits 12 to electrodes disposed in or near the heart. The electronic circuitry is enclosed within a housing made of biocompatible material such as titanium that protects the circuitry from body fluids. The external lead wires, or other conductors to which the lead wires are connected, pass into a connector block or header that is connected to the housing and thence through the wall of the housing to the internal circuitry. The lead wires pass into the housing through a feedthrough assembly that maintains a hermetic seal to prevent the entry of body fluids and insulates the wires from one another and the conductive housing.

In order to transmit and receive telemetry communications, the controller 11 is also interfaced through an encoder/ decoder 17 and driver amplifiers 18 to a coil antenna 20. The controller 31 of the external programmer is similarly interfaced through an encoder/decoder combination 32 and driver amplifiers 33 to a coil antenna 34 that is housed in a portable wand. The implantable device and the external programmer in most telemetry systems communicate by generating and sensing a modulated electromagnetic field in the near-field region with the antennas of the respective devices inductively coupled together. The wand must therefore be positioned in close proximity to the implantable device, typically within a few inches, in order for communications to take place.

Figure 2:
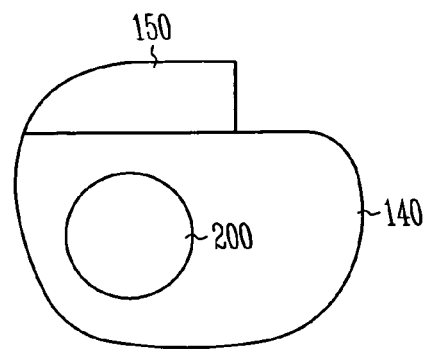
FIG. 2 illustrates an exemplary device housing and header.

FIG. 2 is a more physical depiction of a cardiac rhythm management device showing a housing 140 and a header 150. Shown as contained within the housing 140 in this device is internal circuitry such as that described above with reference to FIG. 1A including a coil antenna 200. Placing the coil antenna 200 in the hermetically sealed metal housing means that the coil antenna does not have to be made of biocompatible material. Metals such as titanium, however, are conductive media that reflect electromagnetic energy at their surfaces except at extremely high frequencies that are not relevant here. At other frequencies, electromagnetic energy penetrates a distance into the metal that increases with wavelength (known as the skin depth). Lower frequency electromagnetic waves can thus propagate through a metal wall with some attenuation if the wall is thin enough, while higher frequency electromagnetic waves, because they do not significantly penetrate into the metal, are completely reflected. This is advantageous in one sense because the conductive housing of the device then effectively shields the internal electronic circuitry from higher frequency electromagnetic interference that could adversely affect device operation. If the coil antenna 200 is also within the conductive housing, however, telemetry must be performed with lower carrier frequencies since the housing effectively acts as a low-pass filter. This necessarily limits the data rate that can be attained by the telemetry link and increases the energy costs for the implantable device when transmitting a given amount of information to the external programmer. Also, even at the lower carrier frequencies, some attenuation of the transmitted signal occurs due to the metal housing. With current device housings, for example, a 100 KHz carrier signal is attenuated by a factor on the order of 16.7 dB. This increases the power requirements for the implantable device in order to transmit an adequate signal and/or limits the range over which telemetry can take place. The latter means that the external programmer wand antenna must be positioned closer to the implantable device, which may be inconvenient for the clinician.

In order to deal with the problem of attenuation of the telemetry carrier signal by the metal housing, it has been proposed to locate the coil antenna 200 of the implantable device in the device header rather than the metal housing. The header is the epoxy or other non-metallic cover which sealingly engages the metallic enclosure of an implantable cardiac device. Because the device header is made of a non-conductive dielectric, it does not attenuate the telemetry carrier signal. An example of this approach is found in U.S. Pat. No. 5,342,408, which is assigned to the assignee of the present application and is hereby incorporated by reference. Referring to FIG. 6 of that document, a front plan view of an implantable cardiac device 12 shows a hermetically sealed enclosure 260 defining a cavity having a perimeter 262 and a header 264 sealingly engaging the perimeter 262. Within the header 264 is an antenna 36 located within the insulative header 264, thereby providing efficient telemetry of data.

The efficiency of the telemetry link is greatly increased with a telemetry coil in the non-conductive device header. The increase in efficiency can be used to reduce the energy expenditure for performing telemetry and/or to increase the telemetry range. For example, if the telemetry range is held constant, the required energy per bit is decreased by an order of magnitude when the coil is in the header rather than the housing. Alternatively, if the energy per bit is held constant, the telemetry range increases by a factor of two or more if the coil is place in the header. Because having the telemetry coil in the header also increases the achievable upper frequency of the carrier, the bandwidth of the telemetry link is increased. The increased bandwidth can be used to allow reduced transmission duty cycles to conserve power, increased data transmission, or more elaborate error detection and correction protocols. Locating the coil antenna in the device header is not without its own problems, however.

Firstly, it is desirable for implantable medical devices to be as small as possible, and the header is generally smaller than the housing. The dimensions of an antenna structure contained within the header are therefore constrained by the smaller size of the space within the header as compared with the device housing. The efficiency of a coil antenna in radiating electromagnetic energy, however, decreases as the size of the coil is made smaller. In certain implementations, for example, it may be desired to incorporate a passive wake-up feature. According to such a design, the programmer transmits a wakeup command with sufficient energy to convert the receiving means of the implanted device from a quiescent state, in which receiving and transmitting circuits are de-energized, to an active state, in which the implanted device and programmer are communicating. However, a relatively large receiving antenna is required in order to couple sufficient electromagnetic energy to the receiving means to facilitate this wakeup function. Such an antenna may be inconsistent with a physically compact implanted cardiac device or with an implanted cardiac device with the antenna in the header.

In order to achieve satisfactory performance with an air-core coil located in the device header, it may therefore be necessary to increase the size of the header so it can accommodate the coil. The present invention provides a way of increasing the efficiency of a coil antenna without increasing its size by disposing a core within the coil made of a magnetically permeable material such as ferrite. A coil antenna with a ferrite core produces increased magnetic flux that can be linked with the antenna of the external programmer which allows the use of a smaller coil within the header to achieve satisfactory performance. A ferrite-core coil, for example, needs to be only approximately one-third the diameter of an air-core coil to achieve similar performance.

Secondly, the device header is not a hermetically sealed compartment, and any material incorporated into the header needs to be biocompatible. Ferrite, however, is not biocompatible. In order to overcome this problem, the ferrite core may be encapsulated in a polyurethane (e.g., Tecothane) coating. The ferrite core may initially be coated with Paralyne before application of the polyurethane. In another embodiment, the entire coil assembly including the windings is encapsulated in polyurethane. In a further modification, the coil is first encapsulated in glass and then in polyurethane. Any of these encapsulation methods yields a biocompatible coil that can be located in the device header and is relatively easy to manufacture.

In an embodiment of a header telemetry coil that has an air core or a ferrite core where only the ferrite core is coated with polyurethane, the coil windings must be biocompatible. Telemetry coil windings in coils located in the hermetically sealed housing have usually been made of copper, but copper is not a biocompatible material and easily corrodes when exposed to the in vivo environment. Platinum is biocompatible and can be used as a winding material, but it has a high resistivity and degrades the performance of the coil. In accordance with another embodiment of the invention, a coil located within a device header is constructed of winding wire having a silver core with a stainless steel (e.g., MP-35N) sheath. Alternatively, the wire core can be made of tantalum which is less expensive but has a slightly higher resistivity. Such winding wire is biocompatible and its resistivity can be matched to circuit requirements by varying the silver (or tantalum) core content.

Figure 3:
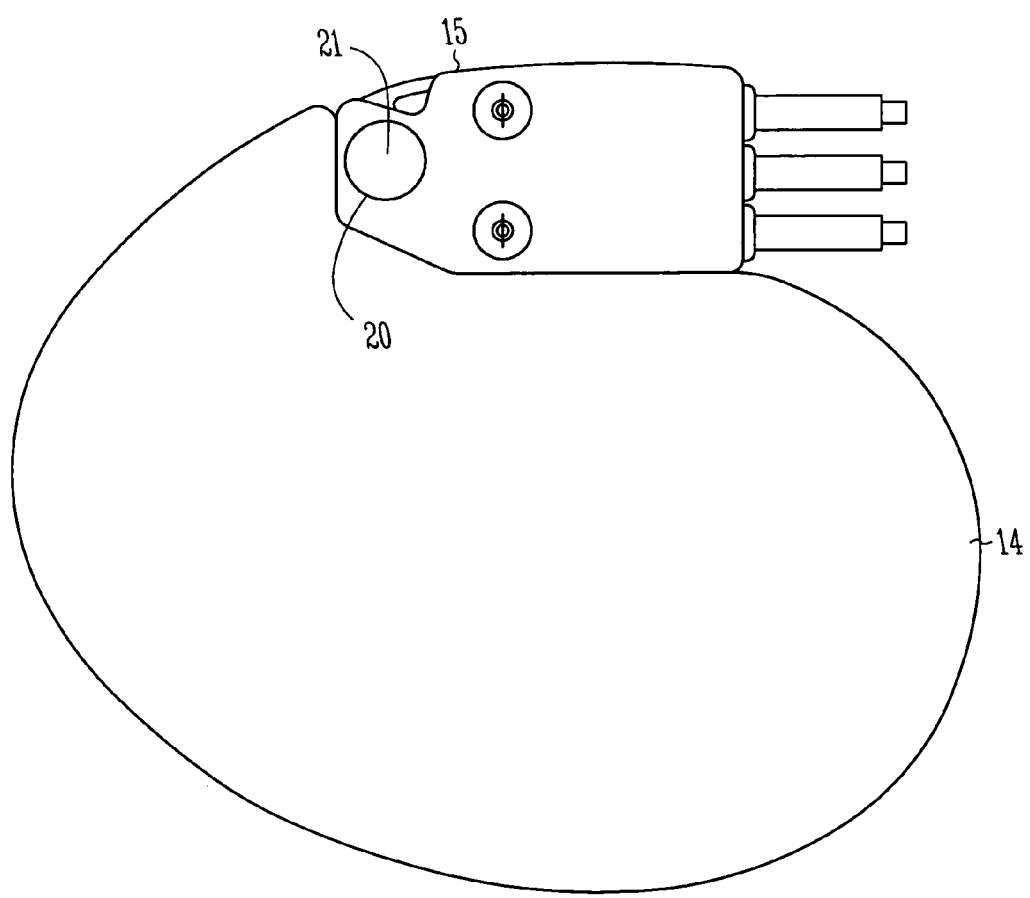
FIG. 3 illustrates a cardiac rhythm management device with a telemetry coil located in the header.

FIG. 3 shows an exemplary cardiac rhythm management device incorporating the present invention. The device has a titanium housing 14 for containing circuit components such as illustrated in FIG. 1A as well as a battery power supply. Connected to the housing 14 is a non-conductive header 15 that receives therapy leads 13 that are electrically connected with the interior of the housing via one or more feedthrough assemblies. A telemetry coil 20 with a ferrite core 21 and encapsulated in polyurethane by one of the methods discussed above is located within the header 15 and electrically connected with the interior of the housing by one or more additional feedthroughs. The coil wires may be wound on a core with a circular cross-section as shown in the figure or a core of rectangular or other cross-section in order to maximize efficiency in an arbitrarily shaped header. Such a device is able to perform more efficient telemetry with lessened energy usage and does not require an inordinate increase in the header volume.

Figure 4:
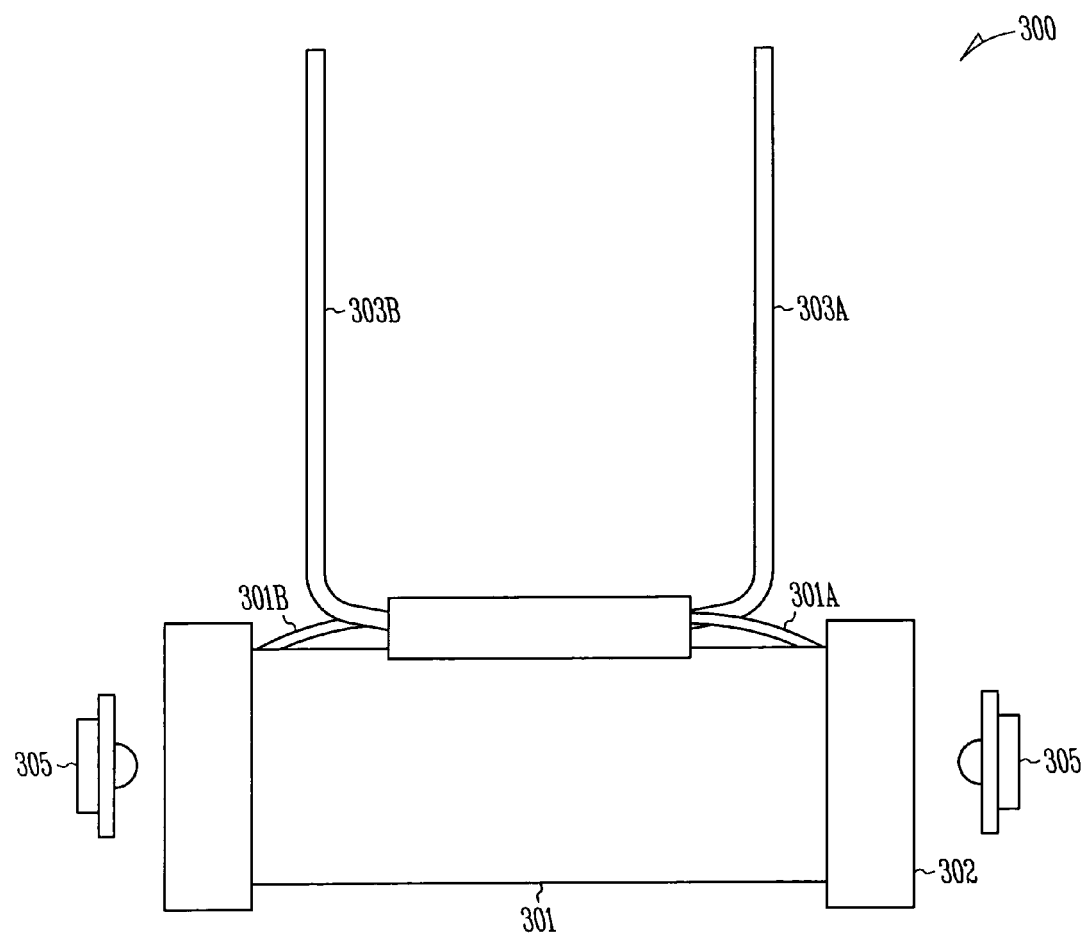
FIG. 4 shows a telemetry coil assembly with a ferrite core.
Figure 5:
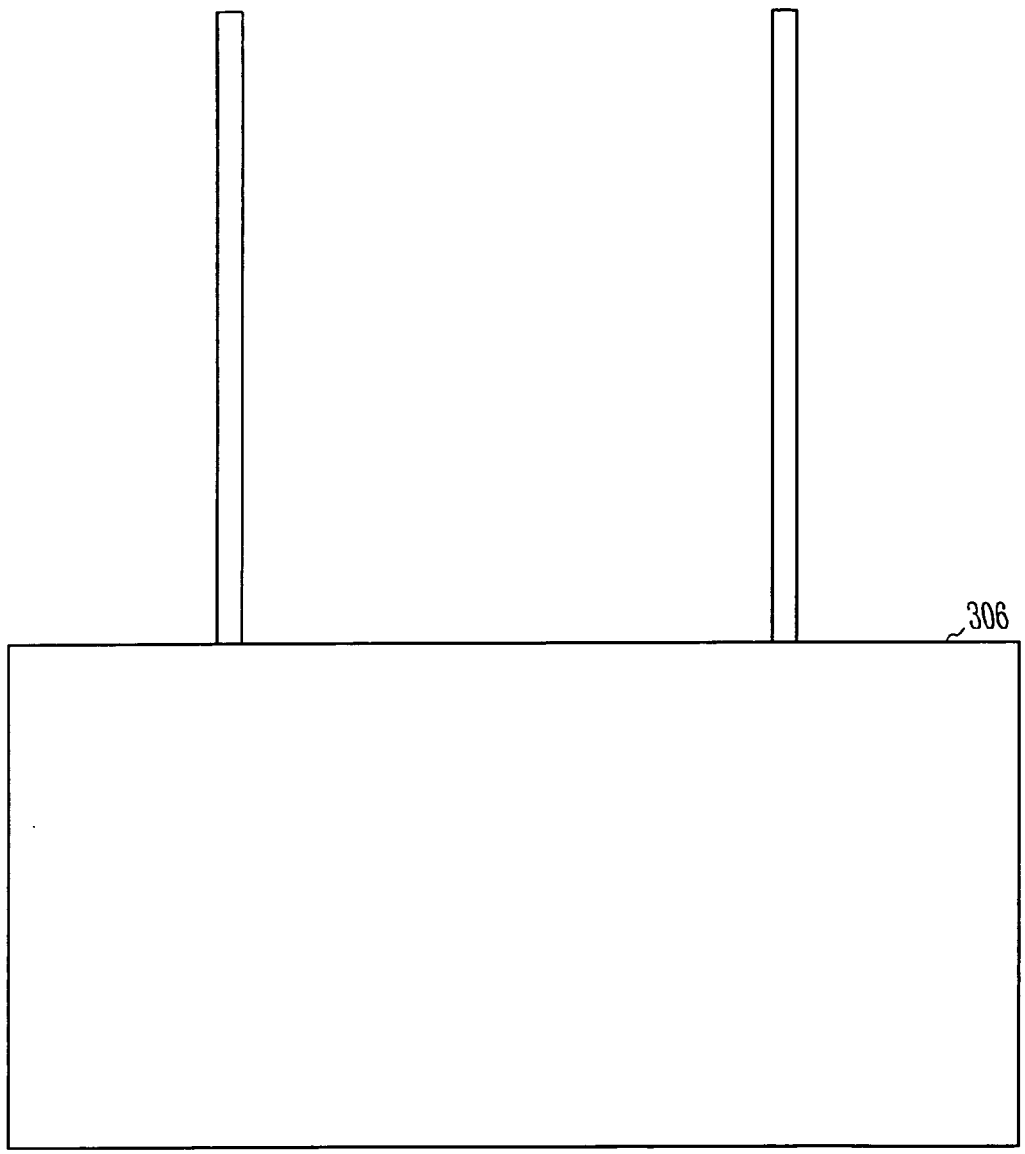
FIG. 5 shows a telemetry coil encapsulated by a polyurethane coating.

FIG. 4 illustrates a particular embodiment of a ferrite-core coil assembly 300. The coil windings 301 are wrapped around a bobbin 302 made of ferrite that constitutes the ferrite core. The ends of the coil wires 301a and 301b are connected to signal wires 303a and 303b that are designed to connect to the internal circuitry via feedthroughs. The entire coil assembly may be coated with polyurethane using an injection molding or other type of molding process. In order for all of the surfaces of the coil assembly to be either coated with polyurethane or made of biocompatible material, biocompatible end caps 305 made of polyurethane or the same mold material may be inserted into the ends of the bobbin 302 and used to support the assembly within the molding vessel. The result is thus a biocompatible coil assembly with a polyurethane coating 306 that covers all of the surfaces (except at the end caps 305) as shown in FIG. 5.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. An implantable medical device, comprising:
   a metal housing for containing electronic circuitry;
   a non-conductive header for receiving external lead wires that are electrically connected to the electronic circuitry within the housing;
   telemetry circuitry for communicating with an external programmer;
   a telemetry coil assembly located in the header and connected to the telemetry circuitry, wherein the coil assembly includes coil windings wrapped around a core made of ferrite, and wherein the core is encapsulated so as to be biocompatible; and,
   wherein the coil assembly is encapsulated with polyurethane and includes a bobbin having biocompatible end caps for supporting the assembly within a molding vessel.

2. The device of claim 1 wherein the core is encapsulated with polyurethane.

3. The device of claim 1 wherein the core is coated with paralyne and then encapsulated in polyurethane.

4. The device of claim 1 wherein the coil assembly is encapsulated in glass and then encapsulated in polyurethane.

5. The device of claim 4 wherein the polyurethane is tecothane.

6. The device of claim 1 wherein the telemetry coil windings are constructed of wire with a silver core and a stainless steel sheath.

7. The device of claim 1 wherein the telemetry coil windings are constructed of wire with a tantulum core and a stainless steel sheath.

8. A method for constructing an implantable medical device, comprising:
   disposing telemetry circuitry in a metal housing;
   assembling a telemetry coil by wrapping coil windings around a ferrite core;
   encapsulating the core in a manner that renders the core biocompatible;
   encapsulating the coil assembly with polyurethane;
   wrapping the coil windings around a bobbin having biocompatible end caps for supporting the assembly within a molding vessel; and,
   disposing the telemetry coil in a non-conductive header and electrically connecting the telemetry coil to the telemetry circuitry within the metal housing.

9. The method of claim 8 further comprising encapsulating the core with polyurethane.

10. The method of claim 8 further comprising coating the core with paralyne and then encapsulating the core in polyurethane.

11. The method of claim 8 further comprising encapsulating the coil assembly in glass and then in polyurethane.

12. The method of claim 11 wherein the polyurethane is tecothane.

13. The method of claim 8 wherein the telemetry coil windings are constructed of wire with a silver core and a stainless steel sheath.

14. The method of claim 8 wherein the telemetry coil windings are constructed of wire with a tantulum core and a stainless steel sheath.

* * * * *

UNITED STATES PATENT AND TRADEMARK OFFICE
CERTIFICATE OF CORRECTION

| | | |
|---|---|---|
| PATENT NO. | : 7,103,413 B2 | Page 1 of 1 |
| APPLICATION NO. | : 10/194401 | |
| DATED | : September 5, 2006 | |
| INVENTOR(S) | : Swanson et al. | |

It is certified that error appears in the above-identified patent and that said Letters Patent is hereby corrected as shown below:

On the Title page, in field (75), in "Inventors", in column 1, line 4, delete "Wyoming" and insert -- Forest Lake --, therefor.

Signed and Sealed this

Twenty-sixth Day of December, 2006

JON W. DUDAS
*Director of the United States Patent and Trademark Office*